United States Patent [19]

Ueyanagi et al.

[11] Patent Number: 4,801,663
[45] Date of Patent: Jan. 31, 1989

[54] ISOCYANURATE POLYISOCYANATE AND ITS USE AS A CURING AGENT FOR A TWO-COMPONENT POLYURETHANE COMPOSITION

[75] Inventors: Kaoru Ueyanagi; Norio Oyabu; Yoshiyuki Asahina, all of Nobeoka, Japan

[73] Assignee: Asahi Kasei Kogyo Kabushiki Kaisha, Osaka, Japan

[21] Appl. No.: 174,919

[22] Filed: Mar. 29, 1988

[30] Foreign Application Priority Data

Apr. 3, 1987 [JP] Japan ................................. 62-81123
Apr. 23, 1987 [JP] Japan ................................. 62-98587
May 11, 1987 [JP] Japan ................................. 62-112624

[51] Int. Cl.$^4$ .............................................. C08G 18/74
[52] U.S. Cl. ................................. 525/528; 252/182.21; 528/73
[58] Field of Search ...................... 528/73; 252/182.21; 525/528

[56] References Cited

U.S. PATENT DOCUMENTS

| | | | |
|---|---|---|---|
| 3,903,127 | 9/1975 | Wagner et al. | 560/335 |
| 3,976,622 | 8/1976 | Wagner et al. | 528/49 |
| 4,324,879 | 4/1982 | Bock et al. | 528/52 |
| 4,345,057 | 8/1982 | Yamabe et al. | 526/247 |
| 4,412,073 | 10/1983 | Robin | 528/52 |
| 4,503,175 | 3/1985 | Houze et al. | 524/39 |
| 4,614,785 | 9/1986 | Richten et al. | 528/67 |

Primary Examiner—Maurice J. Welsh
Attorney, Agent, or Firm—Armstrong, Nikaido, Marmelstein & Kubovcik

[57] ABSTRACT

A novel isocyanurate polyisocyanate is disclosed containing N,N',N''-tris(6-isocyanatohexyl)-isocyanurate in an extremely high proportion and having an extremely low viscosity. The novel isocyanurate polyisocyanate is excellent not only in compatibility with a polyol having a low polarity but also in solubility in a solvent having a low polarity as well as in a polar solvent. The novel isocyanurate polyisocyanate is very useful as a curing agent for a two-component polyurethane composition, especially a two-component polyurethane coating composition. The two-component polyurethane coating composition of the present invention is capable of providing a coat film having extremely excellent properties.

17 Claims, 4 Drawing Sheets

ISOCYANURATE POLYISOCYANATE AND ITS USE AS A CURING AGENT FOR A TWO-COMPONENT POLYURETHANE COMPOSITION

BACKGROUND OF THE INVENTION

1. Field of the Invention

The present invention relates to an isocyanurate polyisocyanate and its use as a curing agent for a two-component polyurethane composition. More particularly, the present invention is concerned with a novel isocyanurate polyisocyanate containing N,N',N''-tris(6-isocyanatohexyl)-isocyanurate in an extremely high proportion and having an extremely low-viscosity so that it is excellent not only in compatibility with a polyol resin having a low polarity and in solubility in a solvent having a low polarity such as n-hexane, methylcyclohexane, mineral turpentine or mineral spirit, but also in heat resistance, as compared to conventional polyisocyanates. The present invention is also concerned with a novel curing agent for a two-component polyurethane composition, which curing agent comprises mainly the present isocyanurate polyisocyanate, wherein the two-component polyurethane composition is represented by a coating composition, an adhesive composition, a casting composition, a potting composition, an elastomer composition, a foaming composition and the like. The present invention is also concerned with a novel two-component polyurethane coating composition comprising the present isocyanurate polyisocyanate and a polyol in a specific proportion, which composition is capable of not only providing an excelent coating performance but also minimizing the use of a highly polar solvent which, when formation of a coating film on a resin substrate is intended, is undesirable from the viewpoints of prevention of blistering and shrinking of the resultant coating film and corrosion of the resin substrate.

2. Discussion of Related art

Heretofore, various aliphatic polyisocyanates have been known. For example, there have been proposed a polyisocyanate having a urethane structure, which is derived from hexamethylene diisocyanate (hereinafter often referred to as "HMDI") (see Japanese Patent Application Publication Specification No. 45-11146), a polyisocyanate having a biuret structure (see U.S. Pat. Nos. 3,903,127 and 3,976,622), a polyisocyanate having an isocyanurate structure (see, for example, U.S. Pat. No. 4,324,879) and a urethane-modified polyisocyanate having an isocyanurate structure (see Japanese Patent Application Laid-open Specificaion No. 57-47321). However, each of these polyisocyanates has a viscosity as high as from 2,000 to several tens of thousands centipoises (cps) as measured at 25° C.

On the other hand, two-component polyurethane coating compositions in which polyol resins such as acrylic polyols, polyester polyols or the like are used as main components and the above-mentioned aliphatic polyisocyanates derived from HMDI are used as curing agents are excellent in weatherability, flexibility, abrasion resistance, etc. and are used in various fields, such as repairing of automobiles, overcoating for architectural structures, etc.

These main components and curing agents are usually dissolved in a solvent before use. However, since the conventional aliphatic polyisocyanates are unsatisfactory with respect to solubility in a solvent having a low polarity such as mineral turpentine, mineral spirit or solvent naphtha, it is necessary to use a solvent having a high polarity such as ethyl acetate, butyl acetate or cellosolve acetate in combination with a solvent having a low polarity.

The use of a solvent having a high polarity in a large amount has drawbacks in that in case it is required to form a multi-layered coating film by repeatedly applying the coating composition, the solvent contained in the later-applied coatings tends to penetrate into the previously formed coating layers so that blistering or shrinking of the surface of the coating film is likely to occur, and that in case the coating composition is applied to a resin substrate, the surface of the resin substrate is likely to be corroded by the solvent contained in the coating composition. As opposed to the above-mentioned polyisocyanates having a viscosity of 2000 or more cps as measured at 25° C., a polyisocyanate derived from HMDI and having an extremely low viscosity has been proposed in U.S. Pat. No. 4,614,785. However, such a low viscosity polyisocyanate has a drawback in that it has a high uretodione content so that free monomeric HMDI is likely to be formed during storage. Therefore, the polyisocyanate is not practically acceptable.

On the other hand, studies on polyols to be used as main components in two-component polyurethane compositions were made with respect to lowering of polarities thereof to improve the solubilities of the polyols in a solvent having a low polarity. However, polyols having low polarities have poor compatibility with conventional polyisocyanates as curing agents, leading to a lowering of the properties of the cured products, such as coating films.

Further, it is noted that in the field of coating compositions, the requirements for the properties of the ultimate coating films have recently become very severe. To meet with such requirements, various proposals have been made. For example, in U.S. Pat. No. 4,345,057 and Japanese Patent Application Laid-open Specification No. 58-34866, there have been proposed two-component polyurethane coating compositions in which fluorine-containing polyols are used as main components and polyisocyanates are used as curing agents. The compositions give ultimate coating films which are very excellent in weatherability. However, in general, the compatibility between the polyisocyanate component and the fluorine-containing polyol component is unsatisfactory. Therefore, the types of polyisocyanate components as well as types of fluorine-containing polyol components which can suitably be used for coating compositions are limited. For example, when the above-mentioned polyisocyanate having a biuret structure or the isocyanurate group-containing polyisocyanate of U.S. Pat. No. 4,324,879 is used with a fluorine-containing polyol, the coating films formed are likely to be white and turbid due to the poor compatibility between the polyisocyanate and the fluorine-containing polyol.

In this connection, it is noted that Japanese Patent Application Laid-open Specification No. 60-203674 has pointed out the poor compatibility between a polyisocyanate curing agent derived from HMDI and a fluorine-containing polyol component, and has proposed the use of a polyisocyanate having cyclohexyl rings as a polyisocyanate component in order to improve compatibility with the fluorine-containing polyol component.

However, the use of a polyisocyanate having cyclohexyl rings prepared from isophorone diisocyanate or the like as a curing agent is disadvantageous in that the operational efficiency becomes poor because the polyisocyanate has an extremely high viscosity and that the flexibility of an ultimate coating film becomes poor. Accordingly, this two-component system is also not satisfactory for use as a coating composition.

Under these circumstances, it has been desired to develop an aliphatic polyisocyanate which is excellent not only in solubility even in a solvent having a low polarity but also in compatibility with a polyol having a low polarity. It has also been desired to develop a two-component polyurethane composition, especially a polyurethane coating composition in which such a polyisocyanate is used as a curing agent.

SUMMARY OF THE INVENTION

The present inventors have made extensive and intensive studies with a view toward developing a novel polyisocyanate derived from HMDI which is excellent not only in solubility in a solvent having a low polarity, but also in compatibility with a polyol having a low polarity. As a result, they have unexpectedly succeeded in producing a novel isocyanurate polyisocyanate having a high N,N',N''-tris(6-isocyanatohexyl)-isocyanurate content and having a viscosity not exceeding 1600 cps, preferably not exceeding 1500 cps, more preferably not exceeding 1400 cps, most preferably not exceeding 1300 cps. They have also found that when such an isocyanurate polyisocyanate is used as a curing agent in combination with a polyol as a main component in a specific proportion in a two-component polyurethane composition, the composition can give an excellent ultimate product, especially an excellent coating film which is greatly improved with respect to weatherability, thermal resistance, adhesion to a substrate, hardness, impact strength, flexibility, elongation, solvent resistance, gloss, surface smoothness and the like. Based on these novel findings, the present invention has been completed.

It is, therefore, an object of the present invention to provide an isocyanurate polyisocyanate which is excellent not only in solubility in a solvent having a low polarity, but also in compatibility with a polyol having a low polarity.

It is another object of the present invention to provide a novel curing agent for a two-component polyurethane composition, which agent is highly compatible with a polyol to be used as a main component of the two-component polyurethane composition, thereby enabling the providing of a two-component polyurethane composition which is capable of giving an excellent ultimate product.

It is a further object of the present invention to provide a novel two-component coating composition in which the present isocyanurate polyisocyanate is used as a curing agent in combination with a polyol as a main component in a specific proportion, and which is capable of giving an excellent coating film which is greatly improved with respect to various properties as mentioned above.

The foregoing and other objects, features and advantages of the present invention will be apparent to those skilled in the art from the following detailed description and appended claims taken in connection with the accompanying drawings.

DETAILED DESCRIPTION OF THE INVENTION

Figure 1:
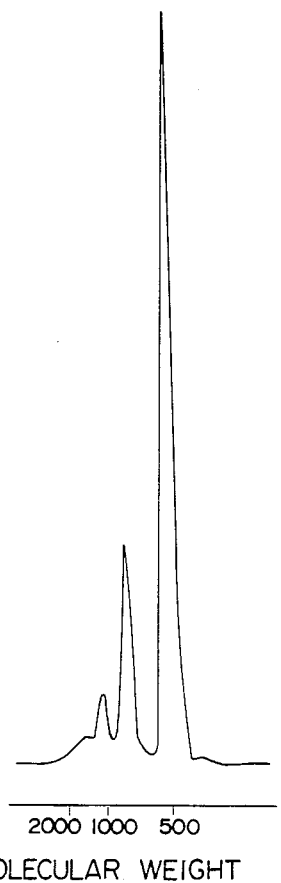
FIG. 1 is a gel permeation chromatographic (GPC) chart of an isocyanurate polyisocyanate of the present invention ([PI-1] obtained in Example 1)

In one aspect of the present invention, there is provided an isocyanurate polyisocyanate comprising:

(a) at least 60% by weight, based on the total weight of the components (a), (b) and (c), of N,N',N''-tris(6-isocyanatohexyl)-isocyanurate, (b) from 0 to 10% by weight, based on the total weight of the components (a), (b) and (c), of N,N'-bis(6-isocyanatohexyl)-uretodione, and (c) 40% by weight or less, based on the total weight of the components (a), (b) and (c), of poly(6-isocyanatohexyl)-isocyanurate, said polyisocyanate having a viscosity of 1600 cps or less as measured at 25° C.

N,N',N''-tris(6-isocyanatohexyl)-isocyanurate, which is hereinafter often referred to simply as "isocyanurate", is represented by the following formula:

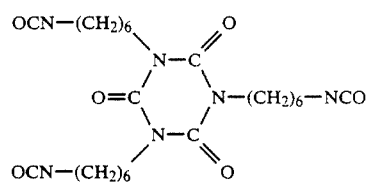

N,N'-bis(6-isocyanatohexyl)-uretodione, which is hereinafter often referred to simply as "uretodione", is represented by the following formula:

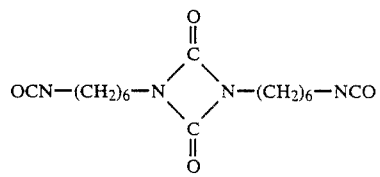

Poly(6-isocyanatohexyl)-isocyanurate, which is hereinafter often referred to simply as "polyisocyanurate", is a mixture of polyisocyanurates represented by the following formula:

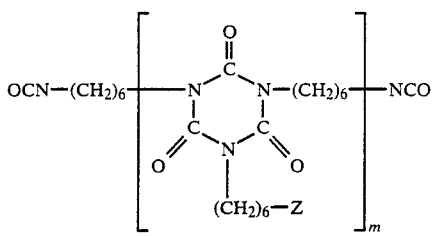

wherein m is an integer of from 2 to about 10 and Z represents —NCO or a group of the formula:

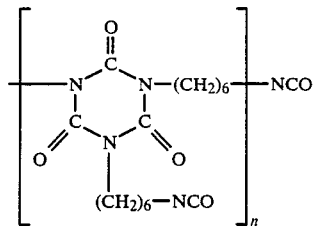

wherein n is an integer of from 1 to 3.

The isocyanurate content as high as at least 60% by weight based on the total weight of the components (a), (b) and (c) and the viscosity as low as 1600 cps or less as measured at 25° C. of the isocyanurate polyisocyanate contribute to a remarkable improvement not only in solubility in a solvent having a low polarity, such as mineral turpentine, but also in compatibility with a polyol having a low polarity, such as a fluorine-containing polyol. The uretodione content as low as 10% by weight or less based on the total weight of the components (a), (b) and (c) contributes to an excellent thermal resistance of the isocyanurate polyisocyanate.

The isocyanurate content, the uretodione content and the polyisocyanurate content of the present isocyanurate polyisocyanate can be determined by gel permeation chromatography. The isocyanurate content is preferably 60 to 95% by weight based on the total weight of the components (a), (b) and (c). The polyisocyanurate content is practically 5 to 40% by weight based on the total weight of the components (a), (b) and (c). The uretodione content is preferably 0 to 5% by weight based on the total weight of the components (a), (b) and (c). When the isocyanurate content is less than 60% by weight, not only the compatibility of the isocyanurate polyisocyanate with a polyol resin having a low polarity but also the solubility of the isocyanurate polyisocyanate in a solvent having a low polarity becomes undesirably poor. On the other hand, it has now been found that an increased isocyanurate content would give better results with respect to the compatibility and the solubility. However, it is not practically advantageous to provide an isocyanurate polyisocyanate having an isocyanurate content exceeding 95% by weight from the viewpoint of ease in production. When the uretodione content exceeds 10% by weight, the thermal stability of the isocyanurate polyisocyanate becomes remarkably low. The NCO content of the isocyanurate polyisocyanate is usually from 22.5 to 24.7% by weight. Further, the isocyanurate polyisocyanate of the present invention is substantially free of monomeric HMDI and solvent.

The viscosity of the present isocyanurate polyisocyanate is preferably 400 to 1600 cps, more preferably 400 to 1500 cps, still more preferably 400 to 1400 cps, most preferably 400 to 1300 cps. When the viscosity of the isocyanurate polyisocyanate exceeds 1600 cps, not only the compatibility with a polyol resin having a low polarity but also the solubility in a solvent having a low polarity becomes undesirably poor. On the other hand, it is not necessarily advantageous to provide an isocyanurate polyisocyanate having a viscosity of less than 400 cps from the viewpoint of the desired yield in polyisocyanate production.

The isocyanurate polyisocyanate of the present invention is prepared by cyclotrimerization of hexamethylene diisocyanate (HMDI) in the presence of a catalyst. In order to obtain an isocyanurate polyisocyanate having a viscosity of 1600 cps or less as measured at 25° C. and an isocyanurate content of at least 60% by weight, the cyclotrimerization reaction is terminated at the time when the conversion of monomeric HMDI into an isocyanurate polyisocyanate has become from about 5 to about 25% by weight, and then the unreacted monomeric HMDI is removed. If the conversion exceeds 25% by weight, the polyisocyanurate content of the reaction mixture increases so that the isocyanurate content decreases, leading to an increase in viscosity of the isocyanurate polyisocyanate. The conversion of the monomeric HMDI into the isocyanurate polyisocyanate (in terms of % by weight) as used herein is determined by the following equation:

$$\text{Conversion} = \frac{\text{Weight of the isocyanurate polyisocyanate produced}}{\text{Weight of the } HMDI \text{ used}} \times 100$$

It is believed that the conversion of the monomeric HMDI into the isocyanurate polyisocyanate is effected through the formation of uretodione, i.e., a cyclic dimer of HMDI which has poor thermal stability. If the reaction is terminated at the time when the conversion is still low, the uretodione content of the product tends to be high. If the uretodione content of the product exceeds 0% by weight, the product is unsatisfactory in thermal stability. Accordingly, it is necessary to select a suitable catalyst, e.g., a compound having no phosphorous atom in order to obtain a product of which the uretodione content is low. Representative examples of suitable catalysts include a hydroxide or organic weak acid salt of a tetraalkylammonium such as tetramethylammonium, tetraethylammonium or tetrabutylammonium, a hydroxide or organic weak acid salt of hydroxyalkylammonium such as trimethylhydroxypropylammonium, trimethylhydroxyethylammonium, triethylhydroxypropylammonium or triethylhydroxyethylammonium, an alkali metal salt of an alkylcarboxylic acid such as acetic acid, caproic acid, octylic acid or myristic acid, a metal salt such as a tin salt, zinc salt or lead salt of the above-mentioned alkylcarboxylic acid, and an aminosilyl group-containing compound such as hexamethyldisilazane.

The catalyst is usually used in an amount of from $10^{-5}$ to 1.0% by weight based on the amount of the HMDI, although the suitable amount varies depending upon the type of the catalyst to be used and the reaction temperature.

On the other hand, as described above, for obtaining the isocyanurate polyisocyanate of the present invention, it is necessary to terminate the conversion reaction of HMDI into an isocyanurate polyisocyanate at an early stage. However, it is difficult to terminate the conversion reaction at an early stage because the isocyanurate group-formation rate at the early stage of the conversion reaction is extremely high. Therefore, the reaction conditions, particularly the amount of the catalyst and manner of addition of the catalyst must be selected strictly. For example, with respect to the manner of addition of the catalyst, the catalyst is preferably added portion-wise to the conversion reaction system at appropriate intervals.

In the conversion reaction, an alcohol may be used as a co-catalyst in an amount of from 0.05 to 1% by weight based on the amount of the HMDI. Representative examples of alcohols useful as the co-catalyst include methanol, ethanol, butanol, ethylene glycol, 1,3-butanediol, neopentyl glycol, 2-ethyl-1,3-hexanediol, trimethylolpropane, polypropylene glycol, phenol and the like. These alcohols may be added simultaneously with addition of the main catalyst to the conversion reaction system. Alternatively, such an alcohol may preliminarily be reacted with HMDI at a temperature of from 40° to 120° C. for 10 minutes to 3 hours, the alcohol being used in an amount of from 0.5 to 5% by weight based on the HMDI, to thereby form urethane bonds. Of these alcohols, polyhydric alcohols such as ethylene glycol, 1,3-butanediol, neopentyl glycol and trimethylolpropane serve not only as a cocatalyst for the conversion reaction, but also as a modifier for the resultant isocyanurate polyisocyanate so as to have urethane bounds (see Japanese Patent Application laid-open Specification No. 57-47321 and U.S. Pat. No. 4,582,888).

For the conversion reaction, a solvent may be used. When a solvent is used, it is of course necessary to use those which are inert to isocyanate groups, such as ethyl acetate, butyl acetate, ethylene glycol dimethyl ether, ethylene glycol monomethyl ether acetate, dioxane, 2-butanone, 2-methyl-4-pentanone, cyclohexanone, benzene, xylene, diethylbenzene, n-hexane, chlorobenzene, dichlorobenzene, decalin and the like. The conversion reaction is usually conducted at a temperature of from 20° to 160° C., preferably from 40° to 120° C. for a period of from several minutes to one day, generally from 20 minutes to 8 hours.

The degree of the conversion can be evaluated by measurement of the NCO content of the conversion reaction mixture, infrared spectrum of the conversion reaction mixture, or refractive index of the conversion reaction mixture.

If the conversion reaction of HMDI into an isocyanurate polyisocyanate proceeds to too high a degree, the content of a polyisocyanurate in the product increases so that the content of an isocyanurate decreases, leading to an increase in viscosity of the product, and as a result, the desired product having excellent properties cannot be obtained. Therefore, it is necessary to terminate the conversion reaction at the time when the converion is from about 5 to about 25% by weight. Incidentally, the NCO content of the reaction mixture is from 43 to 48.8% by weight on a solvent-free basis.

With respect to a method for the termination of the conversion reaction of HMDI into an isocyanurate polyisocyanate at a certain stage, U.S. Pat. No. 4,324,879 discloses a method in which the conversion reaction system is heated to deactivate the catalyst and also discloses a method in which the conversion reaction is terminated by adding a catalyst deactivating agent. However, in the former, the degree of the conversion is still high because the heating for the termination of the conversion reaction at a relatively high temperature serves to advance the reaction, and in the latter, the use of too small an amount of addition of the catalyst deactivating agent is not effective for controlling the conversion to the degree as desired in the present invention. Accordingly, the isocyanurate polyisocyanate obtained according to U.S. Pat. No. 4,324,879 has still a high viscosity, that is 2000 cps or more as measured at 25° C.

By contrast, in the present invention, when the conversion reaches the desired degree, the conversion reaction is terminated by addition of a catalyst deactivating agent such as sulfuric acid, phosphoric acid or the like in an amount of from ⅔ to 5 equivalents, preferably 4/5 to 4 equivalents per equivalent of the catalyst. After termination of the conversion reaction, the unreacted HMDI and solvent, if any, are removed to obtain an isocyanurate polyisocyanate of the present invention. The unreacted HMDI and the solvent are removed, for example, using a film evaporator or by solvent extraction. Because monomeric HMDI is poisonous and has a relatively high vapor pressure, it is necessary to sufficiently remove the unreacted HMDI. In this connection, it is believed that if the monomeric HMDI content of the isocyanurate polyisocyanate is reduced to 0.7% by weight or less, the polyisocyanate is substantially harmless.

If desired, the deactivated catalyst is removed prior to the removal of the unreacted HMDI and the solvent. For example, if the deactivated catalyst remains in the form of a solid insoluble in the solvent, it is likely to adversely affect the properties of the isocyanurate polyisocyanate. Therefore, such deactivated catalyst is removed, for example, by cooling the reaction mixture so that the deactivated catalyst is deposited.

The isocyanurate polyisocyanate of the present invention may be advantageously used as a curing agent for a two-component polyurethane composition. The term "two-component polyurethane composition" as used herein means a set of two separately packed components respectively comprising a polyisocyanate as a curing agent for the composition and comprising a polyol as a main ingredient for the composition. In use, the two components are mixed in order to advance the polyurethane-forming reaction therebetween. Examples of two-component polyurethane compositions include a coating composition, an adhesive composition, a casting composition, a potting composition, an elastomer composition, a foaming composition and the like. If desired, the present curing agent for a two-component polyurethane composition may contain a polyisocyanate other than the isocyanurate polyisocyanate of the present invention so that, for example, cost can be reduced. That is, the present curing agent for a two-component polyurethane composition may comprise from 50 to 100% by weight of the isocyanurate polyisocyanate of the present invention and from 0 to 50% by weight of another polyisocyanate, for example, a conventional aliphatic polyisocyanate. The type and proportion of the polyol to be used together with the present isocyanurate polyisocyanate are the same as will be mentioned later in connection with a two-component polyurethane coating composition.

Accordingly, in another aspect of the present invention, there is provided a method for curing a polyol, which comprises mixing a polyol having at least 2 hydroxyl groups with an isocyanurate polyisocyanate comprising:

(a) at least 60% by weight, based on the total weight of the components (a), (b) and (c), of N,N',N''-tris(6-isocyanatohexyl)-isocyanurate, (b) from 0 to 10% by weight, based on the total weight of the components (a), (b) and (c), of N,N'-bis(6-isocyanatohexyl)-uretodione, and (c) 40% by weight or less, based on the total weight of the components (a), (b) and (c), of poly(6-isocyanatohexyl)-isocyanurate, said polyisocyanate having a viscosity of 1600 cps or less as measured at 25° C., said polyisocyanate being employed in an amount such that the equivalent ratio of the isocyanate groups in said polyisocyanate to the hydroxyl groups in said polyol is from 1:5 to 2:1.

In still another aspect of the present invention, there is provided a two-component polyurethane coating composition comprising:

(A) an isocyanurate polyisocyanate comprising:

(a) at least 60% by weight, based on the total weight of the components (a), (b) and (c), of N,N',N''-tris(6-isocyanatohexyl)-isocyanurate, (b) from 0 to 10% by weight, based on the total weight of the components (a), (b) and (c), of N,N'-bis(6-isocyanatohexyl)-uretodione, and (c) 40% by weight or less, based on the total weight of the components (a), (b) and (c), of poly(6-isocyanatohexyl)-isocyanurate, said polyisocyanate having a viscosity of 1600 cps or less as measured at 25° C., and (B) a polyol having at least 2 hydroxyl groups in one molecule, wherein the equivalent ratio of the isocyanate groups in the component (A) to the hydroxyl groups in the component (B) is from 1:5 to 2:1 and wherein the components (A) and (B) are separately provided and adapted to be mixed in use.

The polyols to be used as the component (B) of the two-component polyurethane coating composition are those which have at least two hydroxyl groups in one molecule. Representative examples of such polyols include an aliphatic hydrocarbon polyol, a polyether polyol, a polyester polyol, a polycarbonate polyol, an epoxy resin having at least 2 hydroxyl groups, an acrylic polyol, a fluorine-containing polyol and the like.

Representative examples of aliphatic hydrocarbon polyols include a polybutadiene having its terminals substituted by hydroxyl groups, and derivatives thereof obtained by hydrogenation and the like. Representative examples of polyether polyols include (1) a polyether polyol prepared by reacting an alkylene oxide such as ethylene oxide, propylene oxide or a mixture thereof with a polyhydric alcohol such as glycerin, propylene glycol or a mixture thereof; (2) a polytetramethylene glycol; (3) a polyether polyol prepared by reacting an alkylene oxide with a polyfunctional compound such as ethylenediamine or ethanolamine; and (4) a so-called polymer polyol prepared by polymerization of acrylamide or the like using the above-mentioned polyether polyol (1) or (3) as a medium. Representative examples of polyester polyols include a polyester polyol prepared by condensation reaction of a dicarboxylic acid or anhydride thereof selected from the group consisting of succinic acid, adipic acid, sebacic acid, a dimer acid, maleic anhydride, phthalic anhydride, isophthalic acid, terephthalic acid and the like or a mixture thereof with a polyhydric alcohol selected from the group consisting of ethylene glycol, propylene glycol, diethylene glycol, butylene glycol, neopentyl glycol, trimethylolpropane, glycerin and the like, a polycaprolactone prepared by ring opening polymerization of $\epsilon$-caprolactone by the use of a polyhydric alcohol, and an ester of a fatty acid having a hydroxyl group with a polyhydric alcohol, such as caster oil or the like, etc. Representative examples of polycarbonate polyols include those which are prepared in a usual manner from, for example an aromatic polyhydric alcohol such as bisphenol A, an aliphatic polyhydric alcohol such as 1,6-hexanediol, an alicyclic polyhydric alcohol and the like.

Representative examples of epoxy resins having at least 2 hydroxyl groups include novolac type, epichlorohydrin type, cyclic oxirane type, glycidyl ether type, glycidyl ester type, polyglycol ether type, glycol ether type, epoxidated aliphatic unsaturated compound type, epoxidated fatty acid ester type, polycarboxylic acid ester type, aminoglycidyl type or resorcin type epoxy resins having at least 2 hydroxyl groups.

The above-mentioned acrylic polyol may be prepared by copolymerization of a copolymerizable (meth)acrylic monomer having at least one active hydrogen atom in one molecule with a monomer copolymerizable therewith [see, for example, Journal of Paint Technology Vol. 43 (563) pp. 68–75 (1971), U.S.A.]. Representative examples of acrylic polyols include acrylic polyol resins which are prepared by copolymerization of an acrylate having an active hydrogen atom, such as 2-hydroxyethyl acrylate, 2-hydroxpropyl acrylate or 2-hydroxybutyl acrylate; a methacrylate having an active hydrogen atom, such as 2-hydroxyethyl methacrylate, 2-hydroxypropyl methacrylate or 2-hydroxybutyl methacrylate; a (meth)acrylic monoester of glycerin; a (meth)acrylic monoester of trimethylolpropane; or a mixture thereof with an acrylate such as methyl acrylate, ethyl acrylate, isopropyl acrylate, n-butyl acrylaate or 2-ethylhexyl acrylate; or with a methacrylate such as methyl methacrylate, ethyl methacrylate, isopropyl methacrylate, n-butyl methacrylate, isobutyl methacrylate, n-hexyl methacrylate, lauryl methacrylate or glycidyl methacrylate; or with a mixture of the above-mentioned (meth)acrylates, in the presence or absence of an unsaturated carboxylic acid such as acrylic acid, methacrylic acid, maleic acid or itaconic acid, an unsaturated amide such as acrylamide, N-methylolacrylamide or diacetone acrylamide, styrene, vinyltoluene, vinyl acetate or acrylonitrile.

Representative examples of fluorine-containing polyols to be used in the present invention include copolymers of a fluoroolefin and a hydroxyl group-containing unsaturated monomer copolymerizable therewith and optionally with other copolymerizable unsaturated monomers. Such copolymers are disclosed, e.g., in Japanese Patent Application Laid-open Specification Nos. 57-34107, 57-34108, 61-200145 and 61-272212, and U.S. Pat. Nos. 4,640,966, 4,529,785, 4,588,781, 4,622,364, 4,544,720, 4,581,412 and 4,667,000.

Representative examples of the above-mentioned fluoroolefin include tetrafluoroethylene, chlorotrifluoroethylene, vinylidene fluoride and hexafluoropropylene. Representative examples of the above-mentioned hydroxyl group-containing unsaturated monomers include hydroxyalkyl vinyl ethers, such as 2-hydroxyethyl vinyl ether and 4-hydroxybutyl vinyl ether. Representative examples of the above-mentioned optional monomers include alkyl vinyl ethers, such as cyclohexyl vinyl ether, ethyl vinyl ether, butyl vinyl ether and hexyl vinyl ether; olefins, such as ethylene, propylene and isobutylene; chloroolefins, such as vinyl chloride and vinylidene chloride; unsaturated carboxylic acids and esters thereof, such as methacrylic acid and methyl methacrylate; vinyl carboxylates, such as vinyl acetate and n-vinyl butyrate.

Representative examples of fluorine-containing polyols to be used in the present invention further include those which are obtained by modifying the above-mentioned copolymer of a fluoroolefin and a hydroxyl group-containing unsaturated monomer copolymerizable therewith by, for example, grafting or blending, as disclosed, e.g., in Japanese Patent Application Laid-open Specification Nos. 59-41321, 59-96177, 60-137950, 61-36374, 61-118466, and 60-1267.

Representative examples of fluorine-containing polyols to be used in the present invention still further include copolymers of an unsaturated monomer having a fluorine-containing group adapted to constitute a pendant group of the copolymer and a hydroxyl group-containing unsaturated monomer copolymerizable therewith and optionally with other copolymerizable unsaturated monomers. These copolymers are disclosed, e.g., in Japanese Patent Application Laid-open Specification Nos. 58-34866, and 61-152771.

Representative examples of unsaturated monomers having a fluorine-containing group adapted to constitute a pendant group of the copolymer include those which are disclosed, e.g., in Japanese Patent Application Laid-open Specification No. 58-34866, represented by the formulae:

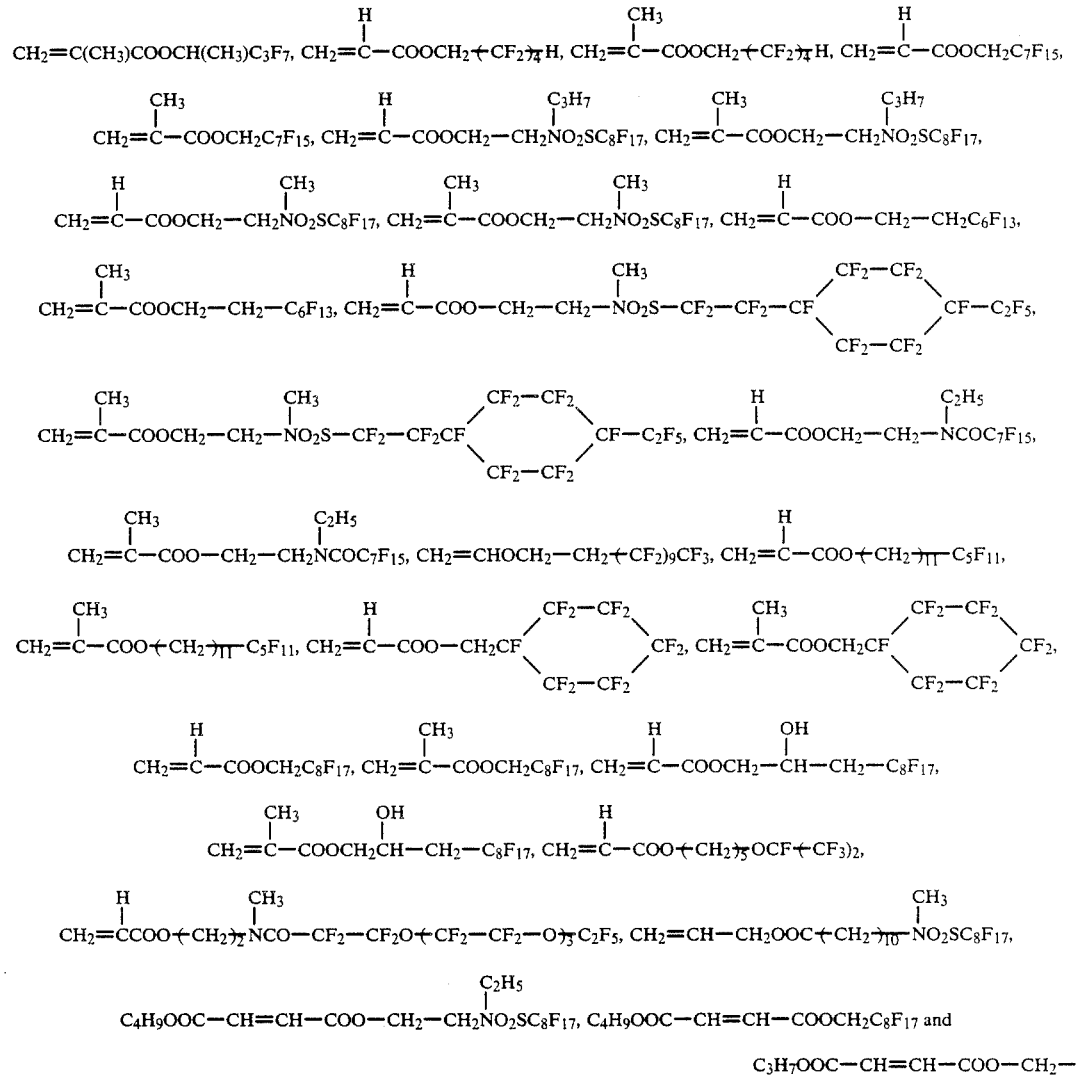

Representative examples of the above-mentioned hydroxyl group-containing unsaturated monomers and other optional monomers include those monomers which are mentioned in connection with the above-mentioned acrylic polyols to be used in the present invention, and also include those monomers which are mentioned in connection with the copolymers of a fluoroolefin, a hydroxyl group-containing unsaturated monomer copolymerizable therewith and other optional copolymerizable monomer, which copolymers are mentioned above to be employable as fluorine-containing polyols.

Representative examples of commercially available fluorine-containing polyols include LUMIFLON LF-100, LUMIFLON LF-200, LUMIFLON LF-300 and LUMIFLON LF-601 (produced and sold by Asahi Glass Co., Ltd., Japan); and K-700 and K-701 (produced and sold by DAINIPPON INK & CHEMICALS, INC., Japan).

These polyols may be used in combination. Of the above-mentioned polyols which may be used as a component (B) for the two-component polyurethane coating composition of the present invention, polyols having a hydroxyl value of from 10 to 300 and a number average molecular weight of from 500 to 30,000 are preferred. More preferred are acrylic polyols, polyester polyols, and fluorine-containing polyols which have a hydroxyl value of from 10 to 300 and a number average molecular weight of from 500 to 30,000. When the hydroxyl value is less than 10, the crosslink density of a polyurethane formed by the reaction of the polyol with the polyisocyanate component becomes low, so that the properties of the resultant polyurethane coating film, particularly solvent resistance, become extremely poor.

On the other hand, when the hydroxyl value is more than 300, the crosslink density increases to too high a degree, so that the mechanical properties of the resultant polyurethane coating film, particularly impact resistance, elongation and the like, become poor. When the number average molecular weight is less than 500, a polyurethane coating film which is excellent not only in hardness but also elasticity is hardly obtainable. On the other hand, when the number average molecular weight is more than 30,000, the viscosity of a polyol resin to be used as a component (B) becomes high and, therefore, the polyol resin becomes uncompatible with a polyisocyanate component so that a uniform polyurethane resin cannot be obtained. This problem can be solved to some extent by diluting the polyol resin with a large amount of a solvent. However, this leads to various disadvantages, such as a difficulty in handling etc.

In the coating composition of the present invention, it is necessary that component (A) and component (B) be used in an amount ratio such that the equivalent ratio of the isocyanate groups in the component (A) to the hydroxyl groups in the component (B) is 1:5 to 2:1, preferably 1:2 to 3:2. If the equivalent ratio is less than 1:5, the properties of the resultant polyurethane coating film, such as solvent resistance, become extremely poor, whereas if the equivalent ratio exceeds 2:1 the properties of the coating film, such as mechanical strength, become decreased.

Further, with respect to the coating composition of the present invention, when the components (A) and (B) are mixed together for use, an appropriate solvent may be employed, if desired. As the solvent, solvents having a low polarity, for example, a hydrocarbon having a low polarity such as mineral turpentine, mineral spirit, cyclohexane, solvent naphtha, toluene, xylene or benzene can advantageously be used. Solvents having a high polarity, for example, ketones such as acetone, methyl ethyl ketone and methyl isobutyl ketone; and esters such as ethyl acetate, butyl acetate and cellosolve acetate, may also be used, if desired, especially when the present coating composition is used for coating of such substrates as metal and concrete because the metal or concrete is resistant to solvents having a high polarity. These solvents may be used alone or in combination.

Still further, the coating composition of the present invention may be mixed with various additives known in the art, such as catalysts, pigments, leveling agents, antioxidants, ultraviolet absorbers, light stabilizers, plasticizing agents and surface active agents, if desired.

The coating composition of the present invention exhibits excellent properties as compared to the conventional coating compositions, due to the excellent properties of the isocyanurate polyisocyanate of the present invention. That is, for example, the present coating composition has great advantages in that it can minimize the use of a highly polar solvent. When formation of a coating film on a resin substrate is intended, the use of a highly polar solvent is undesirable from the viewpoint of prevention of blistering and shrinking of the resultant coating film. Further, by the use of the present coating composition, an excellent coating system free from the danger of corrosion of a resin substrate can be designed.

Further, the present coating composition has advantages in that the isocyanurate polyisocyanate component has a high compatibility with a polyol component and, hence, can produce a coating film having a highly glossy, smooth surface. Further, by the use of a fluorine-containing polyol which is excellent in weatherability, the present coating composition can produce a coating film having an excellent weatherability, due to the excellent compatibility of the present isocyanurate polyisocyanate with the fluorine-containing polyol.

DETAILED DESCRIPTION OF PREFERRED EMBODIMENTS

The present invention will now be described in more detail with reference to the following Examples and Comparative Examples, which should not be construed as limiting the scope of the present invention.

With respect to the Examples and Comparative Examples, the contents of uretodione, isocyanurate and polyisocyanurate were calculated from the respective areas of the corresponding peaks obtained by gel permeation chromatography using the apparatus described below.

Chromatograph: HLC-802A manufactured and sold by TOYO SODA MFG. CO., LTD., JAPAN.
Column: G1000 HXL×1; G2000 HXL×1; G3000 HXL×1, each of which is manufactured and sold by TOYO SODA MFG. CO., LTD., JAPAN.
Carrier: tetrahydrofuran
Detector: differential refractometer
Data processor: CP-8000 manufactured and sold by TOYO SODA MFG. CO., LTD., JAPAN.

The content of the free HMDI in a product was measured by gas chromatography.

The viscosity of a product was measured using EMILA-RHEOMETER (trade name of a rotation viscometer manufactured and sold by EMILA Co., Denmark).

The infrared absorption spectrum (IR) of a product was obtained using a Fourier transform infrared spectrophotometer, FT/IR-5M manufactured and sold by Japan Spectroscopic Co., Ltd., Japan.

EXAMPLE 1

1000 g of HMDI and 300 g of xylene were charged into a four-necked flask having a stirrer, a thermometer and a reflux condenser and the resultant mixture was subjected to polymerization reaction at 60° C. while stirring. During the course of the reaction, 0.3 g of tetramethylammonium caprate as a catalyst was added in four portions at intervals of 30 min.

The NCO content and refractive index of the reaction system were respectively measured by titration and refractometry to monitor the conversion of HMDI into an isocyanurate polyisocyanate. 4 Hours after the start of the reaction at 60° C., the conversion of HMDI into an isocyanurate polyisocyanate reached 21% by weight [NCO content of reaction mixture: 34.2 wt % (44.4% on solvent-free basis)]. The reaction was terminated by adding 0.2 g of phosphoric acid (1.7 equivalent per equivalent of the catalyst). Subsequently, the reaction mixture was further heated at 90° C. for 1 hour and then cooled to room temperature, thereby depositing crystals of the deactivated tetramethylammonium phosphate.

After removal of the deposited crystals by filtration, the reaction mixture was subjected to treatment by means of a falling-film evaporator under conditions of 0.8 mmHg/160° C. and then 0.1 mmHg/160° C. to remove the solvent and unreacted HMDI, thereby obtaining the desired product.

The thus obtained product was a slightly yellowish, transparent liquid and the yield was 210 g. The product had a viscosity of 1300 cps as measured at 25° C. and had an NCO content of 23.5% by weight, a uretodione content of less than 1% by weight, an isocyanurate content of 70% by weight and a free monomeric HMDI content of 0.2% by weight.

The above obtained isocyanurate polyisocyanate is hereinafter referred to as "PI-1".

Figure 2:
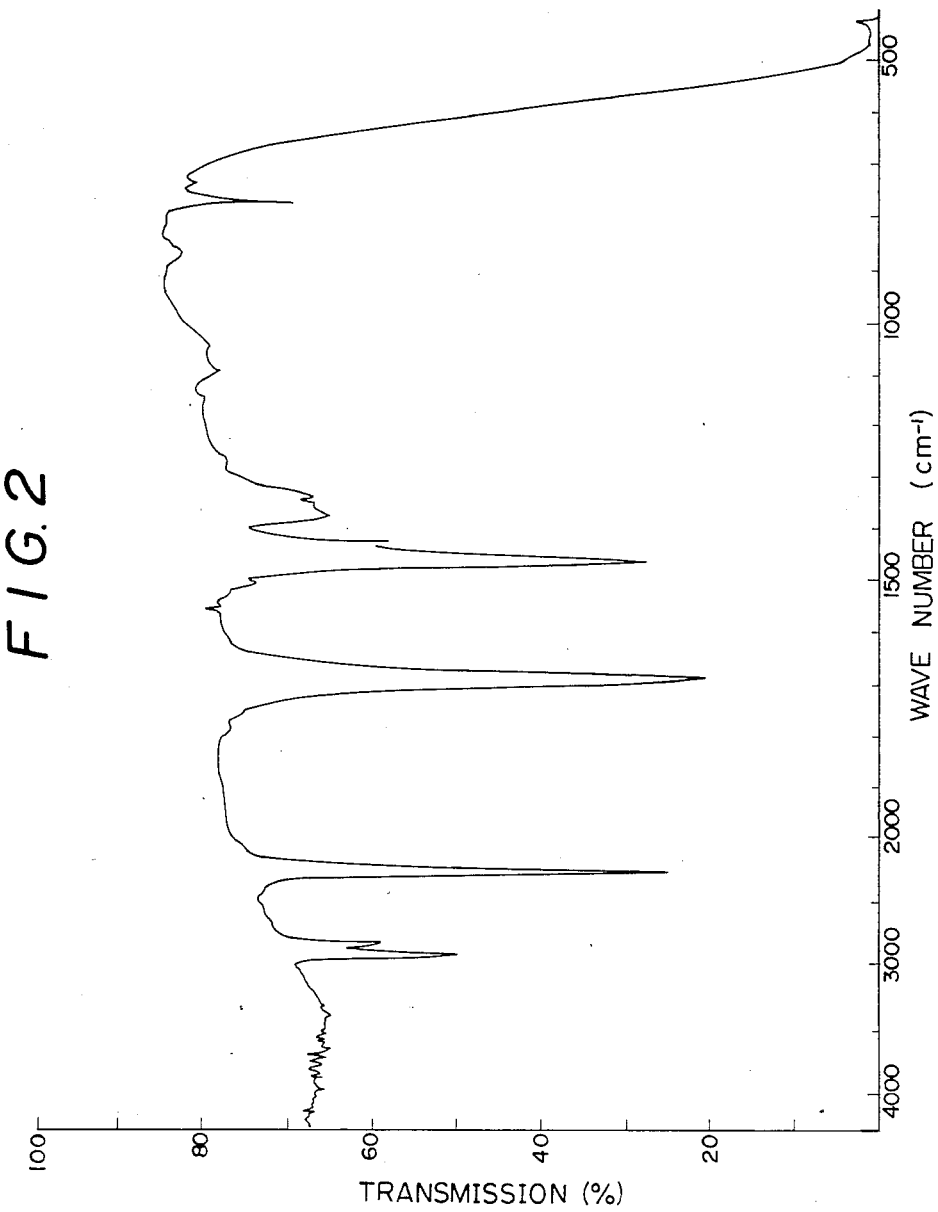
FIG. 2 is infrared spectrum (IR) of the isocyanurate polyisocyanate [PI-1]

The PI-1 was subjected to GPC and IR measurements, and the results are shown in FIG. 1 and FIG. 2, respectively.

EXAMPLE 2

1000 g of HMDI was charged into the same flask as used in Example 1 and polymerization reaction was conducted at 50° C. while stirring. During the course of the reaction, 0.2 g of choline as a catalyst was added in the same manner as described in Example 1.

The NCO content and refractive index of the reaction system were measured in the same manner as in Example 1 to monitor the conversion of HMDI into an isocyanurate polyisocyanate. 3 Hours after the start of the reaction, the conversion of HMDI into an isocyanurate polyisocyanate reached 12% by weight (NCO content of reaction mixture: 46.8 wt %).

The reaction was terminated by adding 0.2 g of phosphoric acid (1.2 equivalent per equivalent of the catalyst), and then the reaction mixture was subjected to treatments for the removal of the deactivated catalyst and unreacted HMDI in the same manner as in Example 1, thereby obtaining the desired product.

The thus obtained product was a slightly yellowish, transparent liquid and the yield was 120 g. The product had a viscosity of 1000 cps as measured at 25° C. and had an NCO content of 23.8% by weight, a uretodione content of less than 1% by weight, an isocyanurate content of 75% by weight and a free monomeric HMDI content of 0.1% by weight.

The above obtained isocyanurate polyisocyanate is hereinafter referred to as "PI-2".

EXAMPLE 3

1000 g of HMDI, 6 g of 1,3-butanediol and 250 g of trimethyl phosphate as a solvent were charged into the same flask as used in Example 1 and preliminary urethanization reaction was conducted at 80° C. for 2 hours.

Then, to the resultant reaction mixture was added 0.5 g of potassium acetate as a catalyst, and polymerization reaction was then conducted at 60° C.

The NCO content and refractive index of the reaction system were respectively measured in the same manner as in Example 1 to monitor the conversion of HMDI into an isocyanurate polyisocyanate. When the conversion of HMDI into an isocyanurate polyisocyanate reached 18% by weight [NCO content of reaction mixture: 36.0 wt % (45.1 wt % on a solvent-free basis)], the reaction was terminated by adding 0.7 g of phosphoric acid (1.4 equivalent per equivalent of the catalyst). Then, the reaction mixture was cooled to room temperature, followed by removing the deactivated catalyst by filtration.

Then the reaction mixture was subjected to treatment for the removal of the solvent and unreacted HMDI in the same manner as in Example 1, thereby obtaining the desired product.

The thus obtained product was a slightly yellowish, transparent liquid and the yield was 180 g. The product had a viscosity of 1200 cps as measured at 25° C. and had an NCO content of 22.6% by weight, a uretodione content of less than 1% by weight, an isocyanurate content of 70% by weight and a free monomeric HMDI content of 0.3% by weight.

The above obtained isocyanurate polyisocyanate is hereinafter referred to as "PI-3".

COMPARATIVE EXAMPLE 1

Polymerization reaction was conducted in substantially the same manner as in Example 1 except that the amount of the catalyst was changed to 0.4 g and that the reaction time was changed to 6 hours.

The NCO content and refractive index of the reaction system were measured in the same manner as in Example 1 to monitor the conversion of HMDI into an isocyanurate polyisocyanate. 6 Hours after the start of the reaction at 60° C., the conversion of HMDI into an isocyanurate polyisocyanate reached 33% by weight [NCO content of reaction mixture: 31.3 wt % (40.8 wt % on a solvent-free basis)]. The reaction was terminated by adding 0.1 g of phosphorous acid (0.6 equivalent per equivalent of the catalyst). The reaction mixture was subjected to treatments for the removal of the deactivated catalyst, solvent and unreacted HMDI in the same manner as in Example 1, thereby obtaining the product.

The thus obtained product was a slightly yellowish, transparent liquid and the yield was 330 g. The product had a viscosity of 2700 cps as measured at 25° C. and had an NCO content of 22.0% by weight, a uretodione content of less than 1 % by weight, an isocyanurate content of 55% by weight and a free monomeric HMDI content of 0.1% by weight.

The above obtained isocyanurate polyisocyanate is hereinafter referred to as "PI-A".

COMPARATIVE EXAMPLE 2

1000 g of HMDI was charged into the same flask as used in Example 1 and 3 g of tributyl phosphine as a catalyst was then added at 70° C. under stirring for polymerization reaction.

The NCO content and refractive index of the reaction system were measured in the same manner as in Example 1 to monitor the conversion of HMDI into an isocyanurate polyisocyanate. 4 Hours after the start of the reaction, the conversion of HMDI into an isocyanurate polyisocyanate had reached 20% by weight (NCO content of reaction mixture: 44.6 wt %). The reaction was terminated by adding 0.48 g of sulfur powder. Then the reaction mixture was subjected to treatments for the removal of the deactivated catalyst and unreacted HMDI in the same manner as in Example 1, thereby obtaining the product.

The thus obtained product was a slightly yellowish, transparent liquid and the yield was 200 g. The product had a viscosity of 900 cps as measured at 25° C. and had an NCO content of 23.4% by weight, a uretodione content of 15% by weight, an isocyanurate content of 65% by weight and a free monomeric HMDI content of 0.3% by weight.

The above obtained isocyanurate polyisocyanate is hereinafter referred to as "PI-B".

COMPARATIVE EXAMPLE 3

Using 350 g of methyl cellosolve acetate as a solvent, 1512 g of HMDI was reacted with 18 g of water at 160° C. The reaction was completed 1 hour after the start of the reaction. Then, the reaction mixture was subjected to treatment for the removal of the solvent and unreacted HMDI by means of a falling-film evaporator in the same manner as in Example 1, thereby obtaining a polyisocyanate having a biuret structure.

The thus obtained polyisocyanate having a biuret structure was a slightly yellowish, transparent liquid and the yield was 420 g. The product had a viscosity of 1200 cps as measured at 25° C. and had a NCO content of 23.7% by weight and a free monomeric HMDI content of 0.2% by weight.

The above-obtained polyisocyanate having a biuret structure is hereinafter referred to as "PI-C".

EXAMPLES 4 to 6 AND COMPARATIVE EXAMPLES 4 to 5

(Thermal stability tests)

The polyisocyanates obtained in Examples 1 to 3 and in Comparative Examples 2 and 3 were separately heated at 140° C. for 1 hour under sealed conditions. After the heating, the increase in quantity of free monomeric HMDI (ΔHMDI) was measured by gas chromatography. The results are shown in Table 1.

From the results, it is apparent that the isocyanurate polyisocyanates of the present invention are excellent in thermal stability.

TABLE 1

| | (Comparison of thermal stability) | |
|---|---|---|
| | Products | ΔHMDI (% by weight based on the product weight) |
| Example 4 | PI-1 | 0.1 wt % |
| Example 5 | PI-2 | 0.1 wt % |
| Example 6 | PI-3 | 0.1 wt % |
| Comparative Example 4 | PI-B | 7.8 wt % |
| Comparative Example 5 | PI-C | 6.5 wt % |

EXAMPLES 7 TO 9 AND COMPARATIVE EXAMPLES 6 TO 7

(Test for solubility in a solvent having a low polarity)

Solutions were prepared by separately dissolving each of products PI-1, PI-2, PI-3, PI-A and PI-C in toluene so that the content of each product in the solution became 10% by weight. n-Hexane was added little by little to 100 parts by weight of each solution while stirring. When the solution became turbid, the addition of n-hexane was stopped. The amount (parts by weight) of the added n-hexane, which is defined as the solubility index, was measured. The results are shown in Table 2.

From the results, it is apparent that the polyisocyanates of the present invention are far more excellent in solubility than the conventional polyisocyanurates.

TABLE 2

| (Comparison of solubilities in a solvent having a low polarity) | | |
|---|---|---|
| | Products | solubility index |
| Example 7 | PI-1 | 80 |
| Example 8 | PI-2 | 80 |
| Example 9 | PI-3 | 80 |
| Comparative Example 6 | PI-A | 50 |
| Comparative Example 7 | PI-C | 15 |

EXAMPLES 10 TO 12 AND COMPARATIVE EXAMPLES 8 AND 9

(Coating characteristics of coating compositions with a solvent having a low polarity)

(EXAMPLES 10 to 12)

Each of products PI-1, PI-2 and PI-3 obtained in Examples 1 to 3 was separately dissolved in a mixed solvent of xylene/mineral spirit (60/40 weight ratio) to obtain solutions each having a concentration of 50%. The solutions were used as curing agents. Each of the curing agents was mixed with ACLYDIC CU-1206 (trade name of a weak solvent-soluble acrylic polyol produced and sold by DAINIPPON INK & CHEMICALS, INC., Japan) so that the NCO/OH equivalent ratio became 1.0. The viscosity of each of the resultant mixtures was adjusted to a value of 12 seconds of Ford cup #4 with a mixed solvent of xylene/mineral spirit (60/40 weight ratio). Each of the mixtures thus adjusted was coated on a mild steel sheet. The resultant coating films were measured with respect to various physical properties and the results are shown in Table 3.

(COMPARATIVE EXAMPLES 8 AND 9)

Each of products PI-A and PI-C obtained in Comparative Examples 1 and 3 was separately dissolved in a mixed solvent of xylene/mineral spirit (60/40 weight ratio) so as to have a concentration of 50% by weight. The resultant solutions were so white and turbid that they could not be used as a curing agent.

TABLE 3

| Example Nos. | 10 | 11 | 12 |
|---|---|---|---|
| Curing agent | PI-1 | PI-2 | PI-3 |
| Gloss[1] | 94% | 93% | 93% |
| Pencil hardness[2] | F | F | F |
| Adhesion[3] | 5B | 5B | 5B |
| Erichsen test[4] | >8 mm | >8 mm | >8 mm |
| Impact resistance[5] | 40 cm | 40 cm | 40 cm |
| Flexing properties[6] | ◎ | ◎ | ◎ |
| Solvent resistance[7] | | | |
| toluene | ◎ | ◎ | ◎ |

TABLE 3-continued

| Example Nos. | 10 | 11 | 12 |
|---|---|---|---|
| Curing agent | PI-1 | PI-2 | PI-3 |
| methyl ethyl ketone | ◉ | ◉ | ◉ |

Note
[1] as measured according to ASTM D523, 60°-60° Gloss
[2] as measured according to ASTM D3363
[3] as measured according to ASTM D3359, Method-B
[4] as measured according to DIN 53156
[5] as measured by a Du Pont impact tester (½" × 500 g) according to JIS K5400
[6] as measured according to ASTM D1737, ¼" acceptable
[7] immersion at 20° C. for 24 hours From Table 3, it is apparent that even when a solvent having a low polarity was used, the curing agents of the present invention prepared from PI-1, PI-2 and PI-3 gave coating films having excellent properties, whereas the conventional polyisocyanates PI-A and PI-C did not even give solutions which can be used as curing agents.

EXAMPLES 13 TO 15

(Formation of coating films on resin substrates)

Each of the solutions for coating which were prepared in Examples 10 to 12 was separately applied to acrylonitrile-butadiene-styrene copolymer (ABS resin) substrates, acrylonitrile-styrene copolymer (AS resin) substrates, polystyrene substrates and polycarbonate substrates, and dried. Then, the surfaces of the coating films were observed. The results are shown in Table 4.

As shown in Table 4, each coating film formed on each resin substrate exhibited excellent surface characteristics such as excellent smoothness and excellent adhesion. Further, the resin substrates exhibit no unfavorable change because the solvents used are those having a low polarity.

TABLE 4

(Surface characteristics of coating films formed on resin substrates)

| Example Nos. | 13 | 14 | 15 |
|---|---|---|---|
| Curing agent | PI-1 | PI-2 | PI-3 |
| ABS resin | ◉ | ◉ | ◉ |
| AS resin | ◉ | ◉ | ◉ |
| Polystyrene | ◉ | ◉ | ◉ |
| Polycarbonate | ◉ | ◉ | ◉ |

◉: excellent in smoothness and adhesion

COMPARATIVE EXAMPLES 10 TO 11

(Criticality of the NCO/OH equivalent ratio)

Solutions for coating were prepared in substantially the same manner as in Example 10 except that the NCO/OH equivalent ratios were changed to 0.1 and 3.0, and the solutions were separately applied to a mild steel sheet, thereby forming coating films. The properties of the resultant coating films were measured. The results are shown in Table 5.

From Table 5, it is apparent that the coating films obtained from the coating composition solutions in which the NCO/OH ratios are outside the range of 1:5 to 2:1 are poor in various properties.

TABLE 5

| Comparative Example | 10 | 11 |
|---|---|---|
| NCO/OH ratio | 0.1 | 3.0 |
| Gloss[1] | 90 | 91 |
| Pencil hardness[2] | B | 6B |
| Adhesion[3] | 0B | 0B |
| Erichsen test[4] | 2 mm | >8 mm |
| Impact resistance[5] | 10 | 40 |

TABLE 5-continued

| Comparative Example | 10 | 11 |
|---|---|---|
| NCO/OH ratio | 0.1 | 3.0 |
| Flexing properties[6] | X | X |
| Solvent resistance[7] | | |
| toluene | X | △ |
| methyl ethyl ketone | X | X |

Note
[1] as measured according to ASTM D523, 60°-60° Gloss
[2] as measured according to ASTM D3363
[3] as measured according to ASTM D3359, Method-B
[4] as measured according to DIN 53156
[5] as measured by a Du Pont impact tester (½" × 500 g) acording to JIS K5400
[6] as measured according to ASTM D1737, ¼" acceptable
[7] immersion at 20° C. for 24 hours

EXAMPLE 16

The isocyanurate polyisocyanate obtained in Example 1 was blended with LUMIFLON LF-601 (a fluorine-containing polyol for a coating composition produced and sold by Asahi Glass Co., Ltd., Japan) so that the NCO/OH ratio became 1 and the resultant blend was applied to a glass substrate to form a coating film having a thickness of 100μ in the dry state. Then the coating film was dried at 20° C. under 65RH for 7 days. The dried coating film was observed with respect to its transparency. The result is shown in Table 6. As shown in Table 6, the coating film was transparent and had no haze.

EXAMPLES 17 AND 18

Substantially the same procedure as in Example 16 was repeated except that the isocyanurate polyisocyanates respectively obtained in Examples 2 and 3 were employed in place of the isocyanurate polyisocyanate obtained in Example 1. The results are shown in Table 6.

COMPARATIVE EXAMPLES 12 AND 13

Substantially the same procedure as in Example 16 was repeated except that the polyisocyanates respectively obtained in Comparative Examples 1 and 3 were employed in place of the isocyanurate polyisocyanate obtained in Example 1. The results are shown in Table 6.

TABLE 6

(Comparison of polyisocyanurates with respect to compatibility with fluorine-containing polyol[1] in terms of transparency of ultimate coating film)

| Example Nos. | Polyisocyanate employed | Transparency of coating film |
|---|---|---|
| Example 16 | PI-1 | ◉ |
| Example 17 | PI-2 | ◉ |
| Example 18 | PI-3 | ◉ |
| Comparative Example 12 | PI-A | X |
| Comparative Example 13 | PI-C | X |

Note
[1]: LUMIFLON LF-601
◉: colorless transparent
X: white turbid coating film

From the results, it is apparent that the isocyanurate polyisocyanates of the present invention are excellent in compatibility with a fluorine-containing polyol over the conventional polyisocyanates.

EXAMPLE 19 AND COMPARATIVE EXAMPLE 14

(Coating characteristics of coating compositions with a polar solvent)

(EXAMPLE 19)

The polyisocyanate PI-1 obtained in Example 1 was dissolved in a mixed solvent of butyl acetate/ethyl acetate/toluene/xylene/cellosolve acetate (30/20/30/15/5 weight ratio) to obtain a solution having a concentration of 50% by weight. The solution was used as a curing agent. The curing agent was mixed with ACLYDIC A-801 (trademark of an acrylic polyol produced and sold by DAINIPPON INK & CHEMICALS, INC., Japan) so that the NCO/OH equivalent ratio became 1.0. The viscosity of the resultant mixture was adjusted to a value of 12 seconds of Ford cup #4 with the same mixed solvent as used above. The mixture thus adjusted was applied separately to various substrates to obtain coating films. Then, the coating films were examined with respect to various properties.

(COMPARATIVE EXAMPLE 14)

Substantially the same procedure as described in Example 19 was repeated, except that the polyisocyanate PI-A obtained in Comparative Example 1 was used in place of PI-1, to thereby obtain coating films. The coating films were examined, and the results are also shown in Table 7.

TABLE 7

Figure 3:
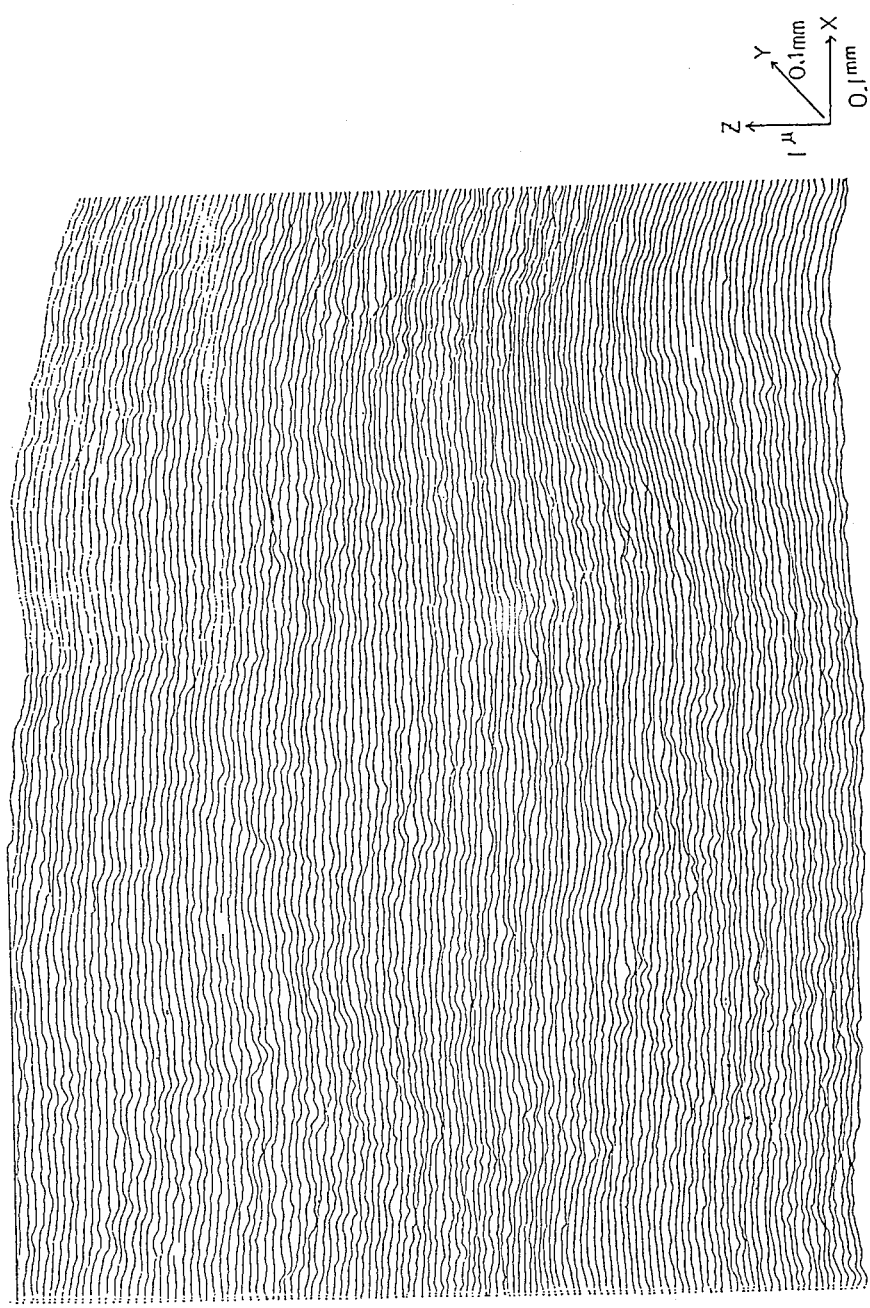
FIG. 3 is a topographic chart showing the surface profile of a coating film prepared from the coating composition of the present invention (Example 19)
Figure 4:
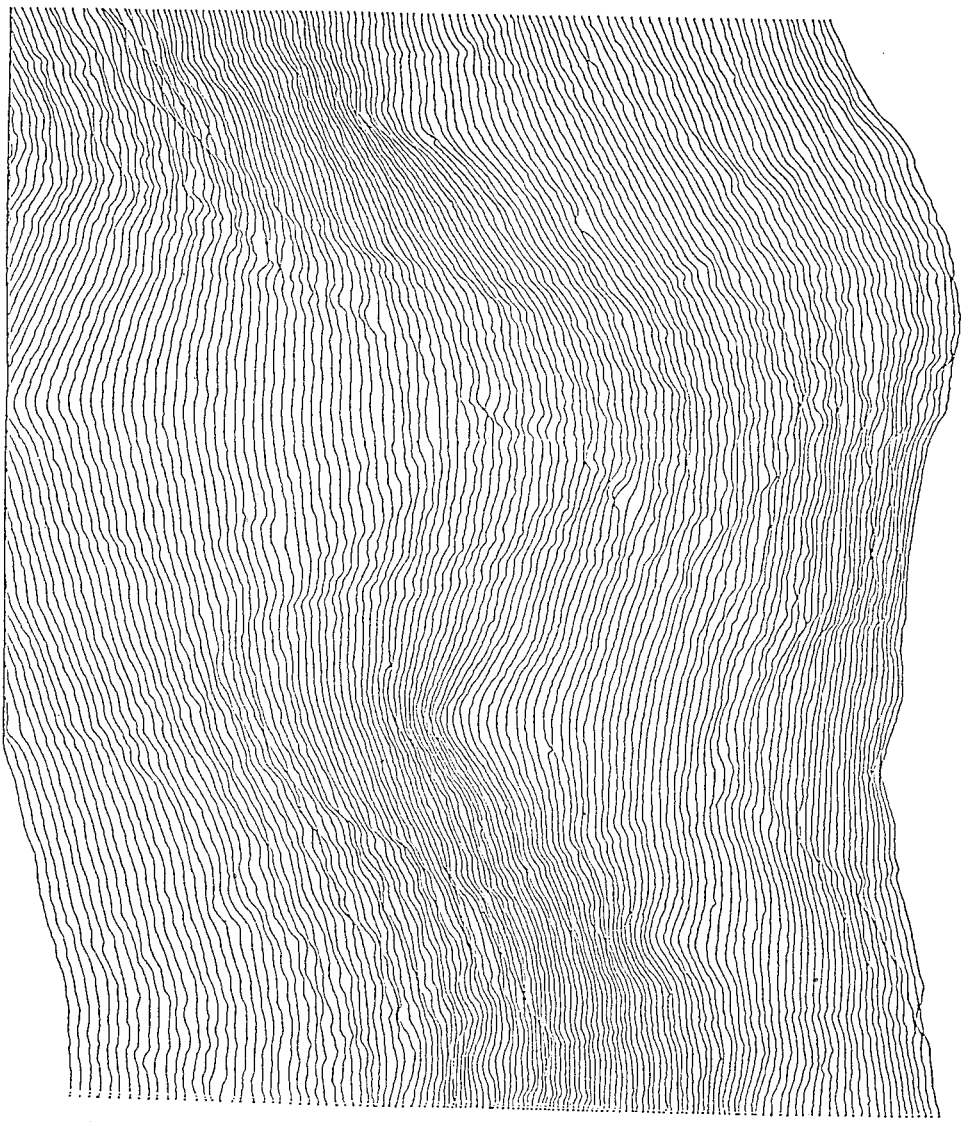
FIG. 4 is a topographic chart showing the surface profile of a coating film prepared from a conventional coating composition (Comparative Example 14).

| Curing agent | | Example 16 PI-1 | Comparative Example 12 PI-A |
|---|---|---|---|
| Curing characteristics | Remaining ratio[1] | | |
| | 16 hrs after application | 62% | 53% |
| | 1 day after application | 77 | 64 |
| | 2 days after application | 90 | 85 |
| | 3 days after application | 93 | 92 |
| | 5 days after application | 95 | 95 |
| Properties | Pencil hardness[2] | HB | HB |
| | Adhesion[3] | | |
| | Steel sheet | 5B | 5B |
| | Aluminum sheet | 4B-5B | 0B-1B |
| | Solvent resistance[4] | | |
| | toluene | ⊚ | ⊚ |
| | methyl ethyl ketone | ⊚ | ⊚ |
| Appearance | Gloss[5] | | |
| | 60°-60° Gloss | 97% | 94% |
| | 20°-20° Gloss | 80 | 73 |
| | Surface profile[6] | as shown FIG. 3 | as shown FIG. 4 |
| Weatherability | Retention of gloss (Accelerated[7] weathering test) Exposure time: | | |
| | 1000 hrs | 100% | 100% |
| | 1500 hrs | 100 | 99 |
| | 2000 hrs | 100 | 93 |
| | 2500 hrs | 95 | 80 |

Note
[1]Each of the coating films was separately cured for different periods of time after application, and then immersed in acetone and allowed to stand at 20° C. for 24 hours. The remaining ratio of the coating film (% by weight) was measured (for this test, coating films were formed on glass plates).
[2]as measured according to ASTM D3363 (for this test, coating films were formed on steel sheets).
[3]as measured according to ASTM D3359, Method-B
[4]immersion at 20° C. for 24 hours (for this test, coating films were formed on steel sheets and aluminum sheets)
[5]as measured according to ASTM D523, 60°-60° Gloss and 20°-20° Gloss (for this test, coating films were formed on steel sheets)
[6]FIG. 3 is a topographic chart showing the surface profile of a coating film prepared from the coating composition of the present invention (Example 19), which chart was obtained using a scanning surface gauge "Surfcom 554AD" (manufactured by Tokyo Seimitsu Co., Ltd., Japan); and FIG. 4 is a topographic chart showing the surface profile of a coating film prepared from the conventional coating composition (Comparative Example 14), which chart was obtained using the same gauge as employed for obtaining the chart shown in FIG. 3 (for this test, coating films were formed on steel sheets).
[7]as measured according to ASTM G-53 (for this test, coating films were formed on steel sheets).

From Table 7, it is apparent that even in the case where a solvent having a high polarity is used for the coating composition, the coating films obtained from the present coating composition exhibit rapid setup and are very excellent in adhesion to a metallic substrate, gloss, particularly 20°-20° gloss, and weatherability. The coating films are also excellent in other properties such as impact strength and flexing properties. Further, it is understood from FIG. 3 that in addition to the above-mentioned excellent properties, the coating film prepared from the present coating composition has an excellent surface profile as demonstrated in FIG. 3, in which the scanning lines representing the profile of the coating film are nearly straight. This means that the coating film has excellent smoothness. Whereas, in FIG. 4 showing the surface topographic chart of the coating film obtained from the conventional polyurethane coating composition, the scanning lines which show the surface profile of the coating film are meandering. This means that the coating film has a rough surface.

What is claimed is:

1. An isocyanurate polyisocyanate comprising:
   (a) at least 60% by weight, based on the total weight of the components (a), (b) and (c), of N,N',N"-tris(6-isocyanatohexyl)-isocyanurate,
   (b) from 0 to 10% by weight, based on the total weight of the components (a), (b) and (c), of N,N'-bis(6-isocyanatohexyl)-uretodione, and
   (c) 40% by weight or less, based on the total weight of the components (a), (b) and (c), of poly(6-isocyanatohexyl)-isocyanurate,
   said polyisocyanate having a viscosity of 1600 cps or less as measured at 25° C.

2. The isocyanurate polyisocyanate according to claim 1, wherein the weight proportion of N,N',N"-tris(6-isocyanatohexyl)-isocyanurate (a) relative to the components (a), (b) and (c) is from 60 to 95%, and the weight proportion of poly(6-isocyanatohexyl)-isocyanurate relative to the components (a), (b) and (c) is from 5 to 40%.

3. The isocyanurate polyisocyanate according to claim 1 or 2, having a viscosity of from 400 to 1500 cps as measured at 25° C.

4. The isocyanurate polyisocyanate according to claim 1 or 2, having a viscosity of from 400 to 1400 cps as measured at 25° C.

5. The isocyanurate polyisocyanate according to claim 1 or 2, having a viscosity of from 400 to 1300 cps as measured at 25° C.

6. A method for curing a polyol, which comprises mixing a polyol having at least 2 hydroxyl groups with an isocyanurate polyisocyanate comprising:
- (a) at least 60% by weight, based on the total weight hBbK of the components (a), (b) and (c), of N,N',N''-tris(6-isocyanatohexyl)-isocyanurate,
- (b) from 0 to 10% by weight, based on the total weight of the components (a), (b) and (c), of N,N'-bis(6-isocyanatohexyl)-uretodione, and
- (c) 40% by weight or less, based on the total weight of the components (a), (b) and (c), of poly(6-isocyanatohexyl)-isocyanurate, said polyisocyanate having a viscosity of 1600 cps or less as measured at 25° C., said polyisocyanate being employed in an amount such that the equivalent ratio of the isocyanate groups in said polyisocyanate to the hydroxyl groups in said polyol is from 1:5 to 2:1.

7. The method according to claim 6, wherein the weight proportion of N,N',N''-tris(6-isocyanatohexyl)-isocyanurate (a) relative to the components (a), (b) and (c) is from 60 to 95%, and the weight proportion of poly(6-isocyanatohexyl)-isocyanurate relative to the components (a), (b) and (c) is from 5 to 40%.

8. The metod according to claim 6 or 7, wherein said isocyanurate polyisocyanate has a viscosity of from 400 to 1500 cps as measured at 25° C.

9. The method according to claim 6 or 7, wherein said isocyanurate polyisocyanate has a viscosity of from 400 to 1400 cps as measured at 25° C.

10. The method according to claim 6 or 7, wherein said isocyanurate polyisocyanate has a viscosity of from 400 to 1300 cps as measured at 25° C.

11. The method according to claim 6 or 7, wherein said polyol is at least one member selected from the group consisting of an aliphatic hydrocarbon polyol, a polyether polyol, a polyester polyol, a polycarbonate polyol, an epoxy resin, an acrylic polyol and a fluorine-containing polyol.

12. A two-component polyurethane coating composition comprising:
(A) an isocyanurate polyisocyanate comprising:
- (a) at least 60% by weight, based on the total weight of the components (a), (b) and (c), of N,N',N''-tris(6-isocyanatohexyl)-isocyanurate,
- (b) from 0 to 10% by weight, based on the total weight of the components (a), (b) and (c), of N,N'-bis(6-isocyanatohexyl)-uretodione, and
- (c) 40% by weight or less, based on the total weight of the components (a), (b) and (c), of poly(6-isocyanatohexyl)-isocyanurate, said polyisocyanate having a viscosity of 1600 cps or less as measured at 25° C., and (B) a polyol having at least 2 hydroxyl groups in one molecule, wherein the equivalent ratio of the isocyanate groups in the component (A) to the hydroxyl groups in the component (B) is from 1:5 to 2:1 and wherein the components (A) and (B) are separately provided and adapted to be mixed in use.

13. The two-component polyurethane coating composition according to claim 12, wherein the weight proportion of N,N',N''-tris(6-isocyanatohexyl)-isocyanurate (a) relative to the components (a), (b) and (c) is from 60 to 95%, and the weight proportion of poly(6-isocyanatohexyl)-isocyanurate relative to the components (a), (b) and (c) is from 5 to 40%.

14. The two-component polyurethane coating composition according to claim 12 or 13, wherein said isocyanurate polyisocyanate has a viscosity of from 400 to 1500 cps as measured at 25° C.

15. The two-component polyurethane coating composition according to claim 12 or 13, wherein said isocyanurate polyisocyanate has a viscosity of from 400 to 1400 cps as measured at 25° C.

16. The two-component polyurethane coating composition according to claim 12 or 13, wherein said isocyanurate polyisocyanate has a viscosity of from 400 to 1300 cps as measured at 25° C.

17. The two-component polyurethane coating composition according to claim 12, wherein said polyol is at least one member selected from the group consisting of an aliphatic hydrocarbon polyol, a polyether polyl, a polyester polyol, a polycarbonate polyol, an epoxy resin, an acrylic polyol and a fluorine-containing polyol.

* * * * *

UNITED STATES PATENT AND TRADEMARK OFFICE
CERTIFICATE OF CORRECTION

PATENT NO. : 4,801,663
DATED : January 31, 1989
INVENTOR(S) : Kaoru UEYANAGI et al It is certified that error appears in the above-identified patent and that said Letters Patent is hereby corrected as shown below:

Column 23, line 11, delete "hBbK".

Signed and Sealed this

Seventeenth Day of October, 1989

Attest:

DONALD J. QUIGG

Attesting Officer

Commissioner of Patents and Trademarks